US012583828B2

(12) United States Patent
Guthertz et al.

(10) Patent No.: US 12,583,828 B2
(45) Date of Patent: Mar. 24, 2026

(54) PREPARATION OF AROMATIC CARBONYL COMPOUNDS BY CATALYTIC OXIDATION WITH MOLECULAR OXYGEN

(71) Applicant: BASF SE, Ludwigshafen (DE)

(72) Inventors: Alexandre Guthertz, Ludwigshafen (DE); Sven Rautenberg, Bornheim (DE); Joaquim Henrique Teles, Ludwigshafen (DE); Florian Vogt, Ludwigshafen (DE); Roland Goetz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 844 days.

(21) Appl. No.: 17/798,077

(22) PCT Filed: Feb. 2, 2021

(86) PCT No.: PCT/EP2021/052397

§ 371 (c)(1),
(2) Date: Aug. 7, 2022

(87) PCT Pub. No.: WO2021/160470

PCT Pub. Date: Aug. 19, 2021

(65) Prior Publication Data

US 2023/0150954 A1 May 18, 2023

(30) Foreign Application Priority Data

Feb. 13, 2020 (EP) .................................... 20157137

(51) Int. Cl.
*C07D 271/06* (2006.01)

(52) U.S. Cl.
CPC ................................. *C07D 271/06* (2013.01)

(58) Field of Classification Search
CPC .................................................... C07D 271/06
See application file for complete search history.

(56) References Cited

FOREIGN PATENT DOCUMENTS

| | | | |
|---|---|---|---|
| EP | 1459804 | A1 | 9/2004 |
| WO | WO-2015/185485 | A1 | 12/2015 |
| WO | WO-2019/020451 | A1 | 1/2019 |

OTHER PUBLICATIONS

International Application No. PCT/EP2021/052397, International Search Report and Written Opinion, mailed May 3, 2021.
European Search Report for EP Patent Application No. 20157137.9, Issued on Jul. 8, 2020, 3 pages.
Hirai, et al., "Oxidation of substituted toluenes with molecular oxygen in the presence of N,N', N''-trihydroxyisocyanuric acid as a key catalyst", The Journal of Organic Chemistry, vol. 68, Issue 17, Jul. 29, 2003, pp. 6587-6590.

*Primary Examiner* — Kamal A Saeed
(74) *Attorney, Agent, or Firm* — MARSHALL, GERSTEIN & BORUN LLP

(57) ABSTRACT

The present invention relates to a process for the preparation of aromatic carbonyl compounds of formula I, which can be obtained through reaction of compounds of formula II with molecular oxygen in the presence of a solvent and a catalyst, which is composed of a cobalt(II) salt and N,N',N"-trihydroxyisocyanuric acid (THICA).

15 Claims, No Drawings

PREPARATION OF AROMATIC CARBONYL COMPOUNDS BY CATALYTIC OXIDATION WITH MOLECULAR OXYGEN

CROSS-REFERENCE TO RELATED APPLICATIONS

This is the U.S. national phase of International Application No. PCT/EP2021/052397, filed Feb. 2, 2021, which claims the benefit of European Patent Application No. 20157137.9, filed on Feb. 13, 2020.

The present invention relates to a process for the preparation of aromatic carbonyl compounds of formula I, which can be obtained through reaction of compounds of formula II with molecular oxygen in the presence of a solvent and a catalyst, which is composed of a cobalt(II) salt and N,N',N"-trihydroxyisocyanuric acid (THICA).

I

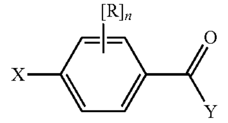

II

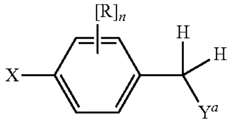

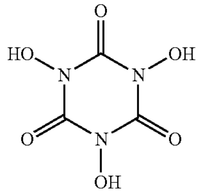

THICA

The process provides access to useful intermediates for the efficient preparation of known benzamide type trifluoromethyl-1,2,4-oxadiazoles, for example compounds disclosed in WO 2015/185485 A1, which are useful for controlling phytopathogenic fungi.

The selective oxidation of alkyl benzene derivatives with molecular oxygen is well known in the prior art. It is also known that this type of oxidation proceeds only sluggishly if the benzene ring carries an electron-withdrawing substituent in para-position to the alkyl group.

The use of catalytic amounts of cobalt(II) salts and THICA, optionally with further additives, for this type of oxidation was described before. Hirai et al. (J. Org. Chemistry 2003, 68, 6587-6590; see also EP 1459804 A1 by the same authors) disclose the oxidation of alkyl benzenes bearing an electron-withdrawing group in para-position, for example p-cyanotoluene, with molecular oxygen (1 atm) in acetic acid and in the presence of THICA (5 mol %) and cobalt(II) acetate (0.5 mol %) at 100° C. Under these conditions, almost quantitative yields of p-cyanobenzoic acid are reported.

In general, the procedures described in the prior art have the disadvantages that they employ relatively high loadings of THICA to achieve satisfactory yields. THICA is comparatively expensive so that the required amount of THICA is a critical parameter for any commercial exploitation.

Further, the processes described in the prior art involve rather long reaction times or the oxygen pressure must be high to achieve good results.

In view of the above, it was an object of the present invention to overcome these disadvantages and to provide an improved and more economical process, which enables the preparation of compounds of formula I, wherein the benzene ring carries an electron-withdrawing substituent in para-position to the alkyl group, on an industrial scale and in high yield and with low amounts of side-products.

The inventors surprisingly found that the oxidation reaction proceeds with high yields and high selectivity, despite low amounts of THICA, if the amount of cobalt(II) salt relative to the amount of THICA is increased. The cobalt(II) salt may be recovered after completion of the reaction without undue effort and may be re-used, while THICA eventually decomposes under the reaction conditions.

Accordingly, the present invention relates to a process for preparing aromatic carbonyl compounds of formula I,

I

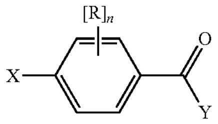

wherein

X is cyano, 5-(trifluoromethyl)-1,2,4-oxadiazole-3-yl, nitro, halogen, $CF_3$, —C(═O)—$C_1$-$C_6$-alkyl, —S(═O)$_2$—$C_1$-$C_6$-alkyl, or —C(═O)—O—$C_1$-$C_6$-alkyl;

R is halogen;

n is 0 or 1;

Y is OH or $C_1$-$C_6$-alkyl;

the process comprising reacting a compound of formula II,

II

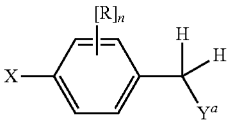

wherein $Y^a$ is hydrogen or $C_1$-$C_6$-alkyl, and wherein the variables X, R, and n are as defined above for compounds of formula I, with molecular oxygen in the presence of a solvent, a cobalt(II) salt and N,N',N"-trihydroxyisocyanuric acid; and wherein the solvent is propionic acid or acetic acid; at a temperature between 70° C. and 200° C.; and whereas the process is characterized in that the amount of N,N',N"-trihydroxyisocyanuric acid is less than 2 mol %, based on the amount of compound II, and in that the molar ratio of the cobalt atoms to N,N',N"-trihydroxyisocyanuric acid is at least 1.

In a preferred embodiment of the present invention the oxidation is conducted in acetic acid.

In one embodiment of the present invention the oxidation is conducted using 0.1 to 2 mol % of THICA, based on the amount of compound of formula II. Preferably, 0.75 to 2 mol % of THICA is used, based on the amount of compound of formula II.

In one aspect the oxidation is conducted using a molar ratio of the cobalt atoms to THICA, which is in the range of from 1:1 to 10:1; preferably from 1:1 to 6:1; or the molar ratio is at least 2; or the molar ratio is in the range of from 2:1 to 10:1; more preferably of from 2:1 to 6:1

In a preferred embodiment the oxidation is conducted using 0.75 to 2 mol % of THICA, based on the amount of compound of formula II, and a cobalt(II) salt, whereas the molar ratio of the cobalt atoms to THICA is in the range of from 2:1 to 6:1.

In a preferred embodiment the oxidation process is conducted at a concentration of at least 7% by weight of compound II, based on the total reaction medium. In another preferred embodiment the oxidation process is conducted at a concentration of at least 10% by weight of compound II, based on the total reaction medium.

In one aspect the oxidation is conducted at a partial pressure of molecular oxygen in the range between 100 and 1000 kPa; preferably between 100 and 500 kPa; more preferably between 100 and 300 kPa.

In one embodiment the reaction temperature of the above process is in the range between 70° C. to 180° C.; preferably in the range of from 90° C. to 160° C.; more preferably in the range of from 100° C. to 130° C.

The reaction is generally carried out within 2 to 12 hours; preferably within 2 to 8 hours; more preferably within 2 to 6 hours.

The process of the present invention is carried out in the presence of a cobalt(II) salt.

Preferably, the anionic counterion in these salts is selected from the group consisting of chloride, bromide, nitrate, phosphate, sulfate, carbonate, perchlorate, triflate, hydroxide, $C_1$-$C_{18}$-alkanoates (for example 2-ethylhexanoate, acetate, stearate, acetylacetonate, or oxalate), aromatic carboxylates (for example benzoate, naphthalene carboxylate).

In a more preferred aspect of the invention the anionic counterion in the cobalt(II) salt is selected from the group consisting of 2-ethylhexanoate, acetate, naphthenate; particularly acetate.

In one aspect of the present invention the variable $Y^a$ in the compounds of formula II is hydrogen and the variable Y in the compounds of formula I is OH.

In one aspect of the present invention the variable n is 1 and R is fluorine.

In a preferred embodiment the variable n is 0.

In one aspect of the present invention the variable X is cyano, 5-(trifluoromethyl)-1,2,4-oxadiazole-3-yl, nitro, fluorine, chlorine, $CF_3$, acetyl, —S(═O)$_2$—$C_1$-$C_6$-alkyl or —C(═O)—O—$C_1$-$C_6$-alkyl in compounds of formulae I and II.

In another aspect of the present invention the variable X is cyano, 5-(trifluoromethyl)-1,2,4-oxadiazole-3-yl, nitro, fluorine, chlorine, acetyl in compounds of formulae I and II. In a preferred aspect of the present invention the variable X is cyano or 5-(trifluoromethyl)-1,2,4-oxadiazole-3-yl in compounds of formula I and II.

In a further aspect of the present invention the variable X is cyano or 5-(trifluoromethyl)-1,2,4-oxadiazole-3-yl, n is 0, the variable $Y^a$ is hydrogen in the compounds of formula II, and the variable Y in the compounds of formula I is OH.

In a further aspect of the present invention the variable X is cyano, n is 0, the variable $Y^a$ is hydrogen in the compounds of formula II, and the variable Y in the compounds of formula I is OH.

In a preferred embodiment (embodiment E.1) of the present invention the amount of N,N',N"-trihydroxyisocyanuric acid is between 0.75 to 2 mol %, based on the amount of compound of formula II.

Embodiment E.2: is based on embodiment E.1, wherein the molar ratio of the cobalt atoms to THICA is in the range of from 2:1 to 6:1.

Embodiment E.3: is based on embodiment E.2, wherein the temperature is between 100° C. and 130° C.

Embodiment E.4: is based on embodiment E.3, wherein the solvent is acetic acid.

Embodiment E.5: is based on embodiment E.4, wherein the concentration of compound of formula II in the reaction mixture is at least 7% by weight.

Embodiment E.6: is based on embodiment E.5, wherein the partial pressure of molecular oxygen is between 100 and 300 kPa.

Embodiment E.7: is based on embodiment E.6, wherein the variable $Y^a$ in the compounds of formula II is hydrogen and the variable Y in the compounds of formula I is OH.

Embodiment E.8: is based on embodiment E.7, wherein the variable n is 0 in compounds of formulae I and II.

Embodiment E.9: is based on embodiment E.7, wherein the variable n is 1 and R is fluorine in compounds of formulae I and II.

Embodiment E.10: is based on embodiment E.6 or E.7, wherein X is cyano or 5-(trifluoromethyl)-1,2,4-oxadiazole-3-yl in compounds of formulae I and II.

The compounds of formula II are either commercially available or they can be prepared from commercially available starting materials using synthetic procedures that are well known to the skilled person in the art. The compounds of formula II, wherein X is 5-(trifluoromethyl)-1,2,4-oxadiazole-3-yl can be obtained from corresponding compounds of formula II, wherein X is cyano, by treatment with hydroxylamine or its hydrochloride salt, in the presence of a base, preferably triethylamine, sodium hydroxide or sodium methylate, in a suitable solvent, such as methanol, ethanol or water, or a mixture of these solvents, at a temperature between 0° C. and 100° C. For related examples see Kitamura, S. et al *Chem. Pharm. Bull.* 2001, 49, 268 or WO 2013/008162 A1 or WO 2015/185485 A1.

In a further embodiment of the present invention the compound of formula I, wherein X is 5-(trifluoromethyl)-1,2,4-oxadiazole-3-yl, n is 0, and Y is OH, is reacted with an amine compound of formula III $$R^1—NH—R^2 \qquad III$$

wherein $R^1$ is $C_1$-$C_6$-alkyl, $C_1$-$C_6$-alkoxy, $C_3$-$C_8$-cycloalkyl, $C_3$-$C_3$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—O—$C_1$-$C_6$-alkyl, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from 0 and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_3$-cycloalkyl, —$NHSO_2$—$C_1$-$C_4$-alkyl, —(C═O)—$C_1$-$C_6$-alkyl, —C(═O)—$C_1$-$C_6$-alkoxy, $C_1$-$C_6$-alkylsulfonyl, hydroxy$C_1$-$C_4$-alkyl, —C(═O)—$NH_2$, C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_1$-cycloalkyl, —C(═O)H, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

to obtain a compound of formula IV

IV

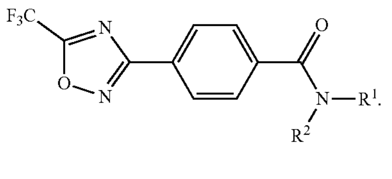

These transformations are also described in WO 2013/008162 A1, WO 2015/185485 A1, or WO 2017/211652 A1 and the references cited therein. The amines of formula III are either commercially available or can be prepared, for example, according to R. C. Larock, Comprehensive Organic Transformations, Verlag Wiley-VCH, 2nd Edition 1999, pages 1929 ff.

In another embodiment, the compound of formula IV is used to obtain a compound of formula V

V

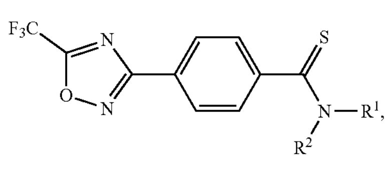

as described in WO 2019/020451 A1 and WO 2017/211649 A1 and the references cited therein.

In a preferred embodiment the variables $R^1$ and $R^2$ in compounds of formula III, IV and V have the following meaning:

$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, OH, $NH_2$, methyl, ethyl, methoxy, trifluoromethyl, trifluoromethoxy, difluoromethyl, difluoromethoxy, and cyclopropyl; and $R^2$ is hydrogen, methyl, or ethyl.

In another preferred embodiment the variables $R^1$ and $R^2$ in compounds of formula III, IV and V have the following meaning:

$R^1$ is methyl, 2-methoxyiminoethyl, bicyclo[1.1.1]pentan-1-yl, 2-fluoro-phenyl, 4-fluoro-phenyl, or 2,4-difluorophenyl; in particular methyl or 2-fluoro-phenyl; and $R^2$ is hydrogen.

In the definitions of the variables given above, collective terms are used which are generally representative for the substituents in question.

The term "$C_n$-$C_m$" indicates the number of carbon atoms possible in each case in the substituent or substituent moiety in question.

The term "halogen" refers to fluorine, chlorine, bromine and iodine.

The term "oxo" refers to an oxygen atom ═O, which is bound to a carbon atom or sulfur atom, thus forming, for example, a ketonyl —C(═O)— or sulfinyl —S(═O)— group.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2—C_2F_5$, $CF_2—C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2—C_2F_5$, $OCF_2—C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_4$-alkoxyimino" refers to a divalent imino radical ($C_1$-$C_4$-alkyl-O—N═) carrying one $C_1$-$C_4$-alkoxy group as substituent, e.g. methylimino, ethylimino, propylimino, 1-methylethyl-imino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N═) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N═).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N═).

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_6$-alkylamino" refers to an amino group, which is substituted with one residue independently selected from the group that is defined by the term $C_1$-$C_6$-alkyl. Likewise, the term "di$C_1$-$C_6$-alkylamino" refers to an amino group, which is substituted with two residues independently selected from the group that is defined by the term $C_1$-$C_6$-alkyl.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH— group which is bound through the nitrogen. Likewise, the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a ($C_1$-$C_4$-alkyl)$_2$N— group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C═O)—$NH_2$ group.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl).

The terms "—C(═O)—$C_1$-$C_6$-alkyl", "—C(═O)—O—$C_1$-$C_6$-alkyl" and "—C(═O)—$C_3$-$C_{11}$-cycloalkyl" refer to aliphatic radicals which are attached through the carbon atom of the —C(═O)— group.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_3$-cycloalkyl-$C_1$-$C_4$-alkyl; therefore a group which contains an aliphatic and a cyclic moiety both of these moieties may be substituted or unsubstituted independently of each other.

The term "phenyl" refers to an aromatic ring systems including six carbon atoms (commonly referred to as benzene ring.

The term "heteroaryl" refers to aromatic monocyclic or polycyclic ring systems including besides carbon atoms, 1, 2, 3 or 4 heteroatoms independently selected from the group consisting of N, O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

WORKING EXAMPLES

The present invention is further illustrated by means of the following working examples.

Analytical Method:

| | |
|---|---|
| Gas Chromatograph | Agilent 7890B |
| Column: | Rxi-5sil MS (30 m long, 0.25 mm (I.D.), 0.25 μm ($d_f$) |
| Temperature program: | $T_{inj}$ = 250° C., 10 min at 40° C., 10° C. per minute until 190° C.,<br>20° C. per minute until 250° and 7 min at 250° C. |
| Preparation of the sample: | 250 μL of the reaction solution was diluted with 250 μL of DMSO and directly injected into the GC |

Example 1.1) Preparation of 4-cyanobenzoic acid 3 g (25.9 mmol) 4-tolunitrile in 43 mL acetic acid (7% by weight of 4-tolunitrile) was placed in a 100 mL glass round bottom flask, which was equipped with a stirring bar, thermometer, reflux condenser and gas inlet. After addition of 45 mg THICA (0.256 mmol, 1 mol % based on 4-tolunitrile) and 255 mg $Co(OAc)_2 \times 4\ H_2O$ (molar ratio of Co:THICA is 4:1) the reaction mixture was heated to 100° C. under an oxygen atmosphere at 100 kPa. Complete conversion to the title compound was detected after a reaction time of 6 hours with a selectivity of 100%.

Example 1.2) Preparation of 4-cyanobenzoic acid

The procedure of Example 1.1 was repeated, except that 2 molar equivalents of $Co(OAc)_2 \times 4\ H_2O$ was used instead of 4 equivalents, based on THICA (molar ratio of Co:THICA is 2:1). After a reaction time of 6 hours conversion to the title compound was 96% with a selectivity of 100%.

Example 1.3) Preparation of 4-cyanobenzoic acid

The procedure of Example 1.1 was repeated, except that 0.75 mol % of THICA was used, based on 4-tolunitrile and 255 mg $Co(OAc)_2 \times 4\ H_2O$ (molar ratio of Co:THICA is 5.3:1). After a reaction time of 6 hours conversion to the title compound was 94% with a selectivity of 100%.

Example 1.4) Preparation of 4-cyanobenzoic acid (Comparative Example)

The procedure of Example 1.1 was repeated, except that 0.5 molar equivalents of $Co(OAc)_2 \times 4\ H_2O$ was used instead of 4 equivalents, based on THICA (molar ratio of Co:THICA is 1:2). After a reaction time of 6 hours conversion to the title compound was 88% with a selectivity of 100%.

Example 1.5) Preparation of 4-cyanobenzoic acid (Comparative Example)

The procedure of Example 1.1 was repeated, except that 0.5 mol % of THICA was used, based on 4-tolunitrile and 1 molar equivalents of $Co(OAc)_2 \times 4\ H_2O$ was used instead of 4 equivalents, based on THICA (molar ratio of Co:THICA is 1:1). After a reaction time of 6 hours conversion to the title compound was 28% with a selectivity of 100%.

Example 2) Preparation of 4-chlorobenzoic acid 1.7 g (13.4 mmol) 4-chlorotoluene in 19 mL acetic acid (9% by weight of 4-chlorotoluene) was placed in a 100 mL glass round bottom flask, which was equipped with a stirring bar, thermometer, reflux condenser and gas inlet. After addition of 24 mg THICA (0.134 mmol, 1 mol % based on 4-chlorotoluene) and 134 mg $Co(OAc)_2 \times 4\ H_2O$ (molar ratio of Co:THICA is 4:1) the reaction mixture was heated to 115° C. under oxygen at 100 kPa. After a reaction time of 8 hours conversion to the title compound was 93% with a selectivity of 98%.

Example 3) Preparation of 4-methylsulfonylbenzoic acid 4 g (23.5 mmol) 4-methylsulfonyltoluene in 39 mL acetic acid (10% by weight of 4-methylsulfonyltoluene) was placed in a 100 mL glass round bottom flask, which was equipped with a stirring bar, thermometer, reflux condenser and gas inlet. After addition of 41.6 mg THICA (0.235 mmol, 1 mol % based on 4-methylsulfonyltoluene) and 117 mg $Co(OAc)_2 \times 4\ H_2O$ (molar ratio of Co:THICA is 2:1) the reaction mixture was heated to 100° C. under oxygen at 100 kPa. After a reaction time of 7 hours conversion to the title compound was 91% with a selectivity of 100%.

Example 4) Preparation of 4-[5-(trifluoromethyl)-1,2,4-oxadiazol-3-yl]benzoic acid 4 g (17.5 mmol) 3-(p-tolyl)-5-(trifluoromethyl)-1,2,4-oxadiazole in 30 mL acetic acid (13% by weight of 3-(p-tolyl)-5-(trifluoromethyl)-1,2,4-oxadiazole) was placed in a 50 mL glass round bottom flask, which was equipped with a stirring bar, thermometer, reflux condenser and gas inlet. After addition of 31 mg THICA (0.175 mmol, 1 mol % based on 3-(p-tolyl)-5-(trifluoromethyl)-1,2,4-oxadiazole) and 87.3 mg $Co(OAc)_2 \times 4\ H_2O$ (molar ratio of Co:THICA is 2:1) the reaction mixture was heated to 100° C. under oxygen at 100 kPa. Complete conversion to the title compound was detected after a reaction time of 7 hours with a selectivity of 100%.

Example 5) Preparation of Methyl Terephthalate 4 g (26.6 mmol) methyl p-toluate in 44 mL acetic acid (9% by weight of methyl p-toluate) was placed in a 100 mL glass round bottom flask, which was equipped with a stirring bar, thermometer, reflux condenser and gas inlet. After addition of 47 mg THICA (0.266 mmol, 1 mol % based on methyl p-toluate) and 133 mg $Co(OAc)_2 \times 4\ H_2O$ (molar ratio of Co:THICA is 2:1) the reaction mixture was heated to 100° C. under oxygen at 100 kPa. Complete conversion to the title compound was detected after a reaction time of 6 hours with a selectivity of 100%.

The invention claimed is:

1. A process for the preparation of an aromatic carbonyl compound of formula I,

I

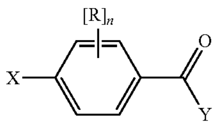

wherein

X is cyano, 5-(trifluoromethyl)-1,2,4-oxadiazole-3-yl, nitro, halogen, $CF_3$, $—C(=O)—C_1\text{-}C_6$-alkyl, $—S(=O)_2—C_1\text{-}C_6$-alkyl, or $—C(=O)—O—C_1\text{-}C_6$-alkyl;

R is halogen;

n is 0 or 1;

Y is OH or $C_1\text{-}C_6$-alkyl;

the process comprising reacting a compound of formula II,

II

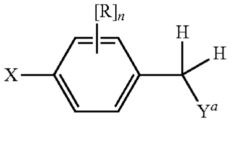

wherein $Y^a$ is hydrogen or $C_1$-$C_6$-alkyl; and wherein the variables X, R, and n are as defined above for compounds of formula I, with molecular oxygen in the presence of a solvent, a cobalt(II) salt, and N,N',N"-trihydroxyisocyanuric acid; and wherein the solvent is propionic acid or acetic acid; at a temperature between 70° C. and 200° C.; and wherein an amount of N,N',N"-trihydroxyisocyanuric acid is less than 2 mol %, based on an amount of compound II, and a ratio of the cobalt atoms to N,N',N"-trihydroxyisocyanuric acid is at least 1.

2. The process according to claim 1, wherein the amount of N,N',N"-trihydroxyisocyanuric acid is between 0.75 to 2 mol %, based on the amount of compound of formula II.

3. The process according to claim 1, wherein the molar ratio of the cobalt atoms to N,N',N"-trihydroxyisocyanuric acid is in the range of from 2:1 to 6:1.

4. The process according to claim 1, wherein the solvent is acetic acid.

5. The process according to claim 1, wherein the temperature is between 100° C. and 130° C.

6. The process according to claim 1, wherein a concentration of compound of formula II in the reaction mixture is at least 7% by weight.

7. The process according to claim 1, wherein a partial pressure of molecular oxygen is between 100 and 300 kPa.

8. The process according to claim 1, wherein the variable $Y^a$ in the compound of formula II is hydrogen and the variable Y in the compounds of formula I is OH.

9. The process according to claim 1, wherein the variable n is 0 in compounds of formulae I and II.

10. The process according to claim 1, wherein the variable n is 1 and R is fluorine in compounds of formulae I and II.

11. The process according to claim 1, wherein X is cyano or 5-(trifluoromethyl)-1,2,4-oxadiazole-3-yl in compounds of formulae I and II.

12. The process according to claim 1, wherein X is cyano or 5-(trifluoro-methyl)-1,2,4-oxadiazole-3-yl, n is 0, and $Y^a$ is hydrogen in the compound of formula II.

13. The process according to claim 12, further comprising reacting the compound of formula I, wherein X is 5-(trifluoro-methyl)-1,2,4-oxadiazole-3-yl, with an amine compound of formula III, $$R^1—NH—R^2 \qquad III$$

wherein $R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—O—$C_1$-$C_6$-alkyl, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from 0 and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$—$C_1$-$C_4$-alkyl, —(C═O)—$C_1$-$C_4$-alkyl, C(═O)—$C_1$-$C_4$-alkyl, $C_1$-$C_6$-alkylsulfonyl, hydroxy$C_1$-$C_4$-alkyl, —C(═O)—$NH_2$, —C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O)H, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

to obtain a compound of formula IV

IV

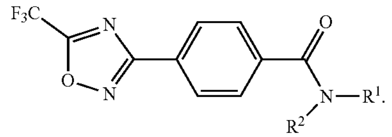

14. The process according to claim 13, further comprising reacting the compound of formula IV to obtain a compound of formula V

V

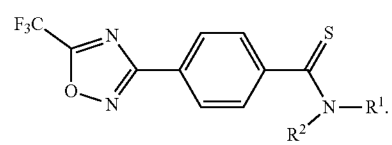

15. The process according to claim 13, wherein in a compound of formula III $R^1$ is methyl, 2-methoxyiminoethyl, bicyclo[1.1.1]pentan-1-yl, 2-fluoro-phenyl, 4-fluoro-phenyl, or 2,4-difluorophenyl; in particular methyl or 2-fluoro-phenyl; and $R^2$ is hydrogen.

* * * * *